United States Patent
Gunzinger et al.

(10) Patent No.: US 8,044,067 B2
(45) Date of Patent: Oct. 25, 2011

(54) ISOQUINOLINES AS IGF-1R INHIBITORS

(75) Inventors: Jan Gunzinger, Couvet (CH); Kurt Leander, Peseux (CH)

(73) Assignee: Analytecon S.A., Couvet (CH)

( * ) Notice: Subject to any disclaimer, the term of this patent is extended or adjusted under 35 U.S.C. 154(b) by 740 days.

(21) Appl. No.: 11/991,431

(22) PCT Filed: Sep. 8, 2006

(86) PCT No.: PCT/IB2006/002473
§ 371 (c)(1),
(2), (4) Date: Mar. 4, 2008

(87) PCT Pub. No.: WO2007/029106
PCT Pub. Date: Mar. 15, 2007

(65) Prior Publication Data
US 2009/0099229 A1     Apr. 16, 2009

(30) Foreign Application Priority Data
Sep. 9, 2005 (WO) .................. PCT/IB2005/002701

(51) Int. Cl.
*C07D 217/00* (2006.01)
*A61K 31/47* (2006.01)

(52) U.S. Cl. ........ 514/307; 514/309; 546/139; 546/141; 546/144

(58) Field of Classification Search .......... None
See application file for complete search history.

(56) References Cited

U.S. PATENT DOCUMENTS
7,875,631 B2 * 1/2011 Gunzinger et al. ........... 514/310

FOREIGN PATENT DOCUMENTS
WO  WO 01/32624       5/2001
WO  WO 2004/054996    7/2004
* cited by examiner

*Primary Examiner* — Zinna Northington Davis
(74) *Attorney, Agent, or Firm* — Harness, Dickey & Pierce, P.L.C.

(57) ABSTRACT

Compounds of the formula (I):

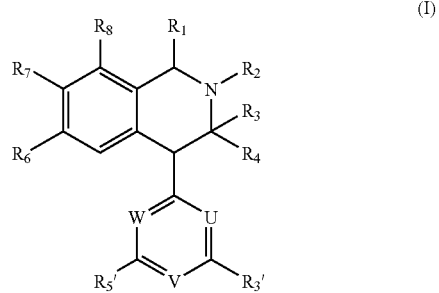

were synthesized. In at least one embodiment, they were found to down-regulate or inhibit the expression or function of the IGF-1 receptor.

24 Claims, No Drawings

ISOQUINOLINES AS IGF-1R INHIBITORS

PRIORITY STATEMENT

This application is a National Phase entry of PCT Application No. PCT/IB2006/002473, filed on Sep. 8, 2006, which claims priority to PCT Application No. PCT/IB2005/002701, filed on Sep. 9, 2005.

FIELD OF THE INVENTION

The present invention relates to novel compounds capable of down-regulating or inhibiting the expression or function of the insulin-like growth factor-1 receptor (IGF-1R). The invention is also directed to pharmaceutical compositions and methods of down-regulating or inhibiting IGF-1R expression or function in order to prevent and/or treat cancer and other abnormal cell growth, and metabolic as well as blood vessel proliferation disorders, in which uncontrolled expression of this receptor is observed.

BACKGROUND ART

The insulin-like growth factor receptor (IGF-1R) is one of 58 trans-membrane tyrosine kinase receptors present in humans [Review: Structure and function of the Type 1 insulin-like growth factor receptor. T. E. Adams et al. *Cell. Mol. Life. Sci.* 57 (2000) 1050-1093; Insulin-Like Growth Factors. Kluwer Academic/Plenum Publishers (2003). Editors: LeRoith, D., Zumkeller, W. and Baxter, R. C.]. Genetic evidence and studies on cells lacking the IGF-1 receptor have demonstrated that it is required for optimal growth, but not an absolute condition for growth [Baserga et al. *Biochim. Biophys. Acta* 1332 (1997) 105-126]. An expression of the IGF-1 receptor protects cells from apoptosis and seems to be a requirement for the establishment and maintenance of the transformed phenotype both in vitro and in vivo [R. Baserga et al. *Biochim. Biophys. Acta* 1332 (1997) 105-126]. Several in vitro and in vivo studies have demonstrated that inhibition of the expression or function of the IGF-1 receptor reverses the transformed phenotype and inhibits tumour cell growth. The techniques used in these studies include neutralizing antibodies [Kalebic et al. *Cancer Res.* 54 (1994) 5531-5534; Arteaga, C. L. et al. *Cancer Res.* 49 (1989) 6237-6241; De Leon, D. D. et al. *Growth Factors* 6 (1992) 327-336], antisense oligonucleotides [Resnicoff et al. *Cancer Res.* 54 (1994) 2218-2222; Andrews, D. W. et al. *J. Clin. Oncol.* 19 (2001) 2189-2200; White, P. J. et al. *Antisense Nucleic Acid Drug Dev.* 10 (2000) 195-203], dominant negative mutants [D'Ambrosio et al. *Cancer Res.* 56 (1996) 4013-4020; Prager, D. et al. *Proc. Natl. Acad. Sci. USA* 91 (1994) 2181-2185; Reiss, K. et al. *Clin. Cancer Res.* 4 (1998) 2647-2655], triple-helix forming oligonucleotides [Rinninsland et al. *Proc. Natl. Acad. Sci. USA* 94 (1997) 5854-5859], antisense mRNA [Nakamura et al., *Cancer Res.* 60 (2000) 760-765] and RNA interference using a double stranded RNA [V. M. Macaulay et al. WO-A-03/100059].

The use of antisense oligonucleotides to inhibit the IGF-1 receptor expression in keratinocytes has been shown to reverse the epidermal hyper proliferation in psoriasis lesions [C. J. Wraight et al. *Nat. Biotechnol.* 18 (2000) 521-526].

Down-regulation of the IGF-1 receptor would possibly also have beneficial effect with respect to diseases such as diabetic retinopathy [L. K. Shawver et al. *DDT* 2 (1997) 50-63] as well as atherosclerosis, restinosis [A. Bayes-Genis et al. *Circ. Res.* 86 (2000) 125-130] and rheumatoid arthritis [J. Pritchard et al. *J. Immunol.* 173 (2004) 3564-3569].

The IGF-1 receptor system is regarded as an attractive target in the prevention and/or treatment of diseases that are dependant on an expression or over-expression of the IGF-1 receptor for their proliferation [L. Long et al. *Cancer Research* 55 (1995) 1006-1009, R. Baserga *TIBTECH* 14 (1996) 150-152; R. Baserga et al. *Endocrine* 7 (August 1997) 99-102; V. M. Macaulay et al. *Annals of Oncogene* 20 (2001) 4029-4040; A. J. Salisbury et al. *Horm. Metab. Res.* 35 (2003) 843-849; Mitsiades, C. S. et al. *Cancer Cell* 5 (2004) 221-230].

A series of substances, named tyrphostins, have been claimed to down-regulate or inhibit the expression of the IGF-1 receptor [M. Parrizas et al. *Endocrinology* 138 (1997) 1427-1433; G. Blum et al. *Biochemistry* 39 (2000) 15705-15712; G. Blum et al. *J. Biol. Chem.* 278 (2003) 40442-40454]. The drawback with the tyrphostins are their low activity in cell systems and that they cross-react with the insulin receptor.

It has been demonstrated [L. Kanter-Lewensohn et al. *Mol. Cell. Endocrinology* 165 (2000) 131-137] that, tamoxifen, at high concentration, has the ability to down-regulate or inhibit the tyrosine phosphorylation of the IGF-1R β-subunit, thereby blocking downstream signalling.

In U.S. Pat. No. 6,337,338 B1, a number of heteroaryl-aryl urea substances are described as antagonists of the IGF-1 receptor. In cell growth inhibition studies on MCF-7 and MCF-10 cell lines the substances showed low activities.

In the patent application WO 02/102804 A1 it is demonstrated that podophyllotoxin, deoxypodophyllotoxin, picropodophyllin and deoxypicropodophyllin are selective and efficient inhibitors of the IGF-1 receptor. Deoxypicropodophyllin has previously [A. Akahori et al. *Chem. Pharm. Bull.* 20 (1972) 1150-1155] been shown to be superior to deoxypodophyllotoxin in retarding the death of mice inoculated with lymphatic leukemia L1210. No mechanism of action, however, was proposed.

In the patent application WO 02/102805 A1 it is shown that also acetylpodophyllotoxin, epipodophyllotoxin, podophyllotoxone and 4'-demethylpodophyllotoxin are potent inhibitors of the IGF-1R phosphorylation.

In two patent applications (WO 03/048133 A1 and WO 02/092599 A1) a number of pyrimidine derivatives are described as modulators of the IGF-1 receptor. However, these pyrimidine derivatives have shown a poor IGF-1R down-regulating activity.

WO 01/32624 (DU PONT PHARM CO) discloses 4-phenyl-substituted tetrahydroisoquinoline compounds. These compounds are useful in the treatment of various neurological and psychiatric disorders, (e.g., ADHD) by blocking the reuptake of norepinephrine, dopamine and serotonin.

WO 2004/054996 (AXELAR AB) refers to compounds belonging to the group of substituted 1-phenyl-tetrahydronaphtalenes and the use thereof as inhibitors of the insulin-like growth factor-1 receptor. Said compounds can be used for treatment of IGF-1R dependent diseases, such as cancer, psoriasis, arteriosclerosis and acromegaly.

WO 02/102804 (KAROLINSKA INNOVATIONS AB) refers to the use of specific cyclolignans, wherein the carbon atoms in positions 9 and 9' have cis configuration, for inhibition of the insulin-like growth factor-1 receptor. Said compounds can be used for treatment of IGF-1R dependent diseases, such as cancer, psoriasis, artherosclerosis and acromegaly. A preferred compound is picropodophyllin.

China Raju B et al., ("Quinone methide initiated cyclization reaction: synthesis of 4-aryl-1,2,3,4-tetrahydroisoquinolines" TETRAHEDRON LETTERS, ELSEVIER, AMSTERDAM, NL, vol. 45, n° 40, 27 Sep. 2004, pp 7487-

7489, XP004561736 ISSN: 0040-4039) discloses the synthesis of 4-aryl-1,2,3,4-tetrahydroisoquinolines in very good yields by in situ generation of p-quinone methides resulting in a novel C—C bond formation.

EP-A-1 113 007 (PFIZER) relates to tetrahydroisoquinoline compounds that are estrogen agonists and antagonists, and the pharmaceutical uses thereof. Said compounds are useful for treating or preventing obesity, breast cancer, osteoporosis, endometriosis, cardiovascular disease, prostatic disease, and the like.

PCT/CH2004/000147 (Analytecon S. A.) provides new heterocyclic compounds with surprisingly improved IGF-1R down-regulating activity.

There is, however, still a need for IGF-1R down-regulating compounds as alternatives to those described in PCT/CH2004/000147 and elsewhere, with e.g. improved aqueous solubility as well as different physical and metabolic properties.

The present invention aims at providing new compounds with high IGF-1R down-regulating activity, wherein the above-identified problems are successfully solved.

SUMMARY OF THE INVENTION

The object set is achieved by the compounds of the following formula (I):

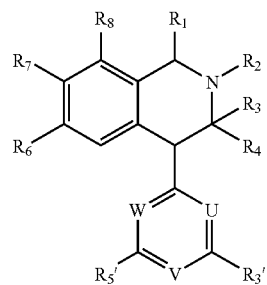

wherein $R_1$ designates hydrogen; OH; CN; trifluoromethyl; $NH_2$; NHCN; $NHCOCH_3$; $NHCOCH_2CH_3$; NHCHO; $NHCOOCH_3$; amino($C_1$-$C_6$) alkyl; amino($C_1$-$C_3$)dialkyl; ($C_1$-$C_6$)alkoxy; ($C_1$-$C_6$) alkyl; carbonyl-$R_9$ wherein $R_9$ designates hydrogen, ($C_1$-$C_6$) alkyl, ($C_1$-$C_6$)alkoxy; ($C_1$-$C_6$)alkyl-$R_{10}$; ($C_1$-$C_6$)alkoxy-$R_{10}$; amino($C_1$-$C_6$)alkyl-$R_{10}$ and amino($C_1$-$C_3$)dialkyl-$R_{10}$ whereby $R_{10}$ designates at least one OMe, OEt, OPr, OIsopropyl, OH, CN, $NH_2$, ester groups with ($C_1$-$C_3$)alkyl, carbonate groups with ($C_1$-$C_3$) alkyl;

$R_2$ designates (when $R_3$,$R_4$ forms a carbonyl group): hydrogen, ($C_1$-$C_6$) alkyl, $CH_2CH_2N(CH_3)_2$, $NH_2$, $NRCH_3$, $N(CH_3)_2$, NHCN, $NHCOCH_3$, $NHCOCH_2CH_3$, NHCHO, $NHCOOCH_3$;

$R_2$ designates (when $R_3$=$R_4$=H): hydrogen, ($C_1$-$C_6$) alkyl, CN, CHO, $COOCH_3$, $COOCH_2CH_3$, $COCH_3$;

$R_3$ and $R_4$ designate hydrogen or $R_3$ and $R_4$ taken together form a carbonyl group;

$R_6$ designates hydrogen, or $R_6$ and $R_7$ taken together form a methylenedioxy group or an ethylenedioxy group;

$R_7$ designates Me, halogen, ($C_1$-$C_4$)alkoxy, ($C_1$-$C_2$)alkoxy partly or fully fluorinated, SMe, SEt, trifluoromethyl, hydrogen or $R_7$ and $R_8$ taken together form a methylenedioxy group or an ethylenedioxy group; if $R_8$ is OH or OX, $R_7$ may be hydrogen;

$R_8$ designates hydrogen, OH, ($C_1$-$C_4$)alkyl, ($C_1$-$C_4$) alkoxy, ($C_1$-$C_2$)alkoxy partly or fully fluorinated, trifluoromethyl, halogen or OX;

$R_3$' and $R_5$' each independently designate OH, Me, Et, OMe, OMe partly or fully fluorinated, trifluoromethyl or halogen;

U designates N or $CR_2$', whereby $R_2$' denotes hydrogen, ($C_1$-$C_4$)alkyl, ($C_1$-$C_4$)alkoxy, trifluoromethyl or halogen;

V designates N or $CR_4$', whereby $R_4$' denotes hydrogen, ($C_1$-$C_6$)alkoxy, ($C_1$-$C_4$)alkoxy partly or fully fluorinated, ($C_1$-$C_6$)alkyl, OH, trifluoromethyl, halogen, or OX;

W designates N or $CR_6$', whereby $R_6$' denotes hydrogen, ($C_1$-$C_4$)alkyl, ($C_1$-$C_4$)alkoxy, trifluoromethyl or halogen;

and wherein OX designates a group capable of conferring a prodrug property as defined below;

and pharmaceutically acceptable salts thereof, where applicable (see below);

provided that when:

$R_1$ is H, $R_2$ and $R_7$ are Me, $R_3$, $R_4$, $R_6$, $R_8$ and $R_4$' are H, $R_3$' and R5' must not be F; or $R_1$, $R_2$ and $R_7$ are Me, $R_3$, $R_4$, $R_6$, $R_8$ and $R_4$' are H, $R_5$' must be different from F; or $R_1$ is H, $R_2$ and $R_7$ are Me, $R_3$, $R_4$, $R_6$, $R_8$ are H, $R_4$' or $R_5$' must be different from F.

Preferred embodiments of the compounds of formula (I) are derivable from the following description.

Further objects of the invention are the use of the compounds (I) in the manufacture of a medicament, particularly for the prevention or treatment of diseases in which the down-regulation or inhibition of the expression or function of the IGF-1 receptor is considered beneficial and pharmaceutical compositions containing a compound (I).

DETAILED DESCRIPTION OF THE INVENTION

As used herein, the term "comprise" is generally used in the sense of include, that is to say permitting the presence of one or more features or components.

The compounds of formula (I) are derivatives of 4-aryl-1,4-dihydro-3(2H)-isoquinolinones and 4-aryl-1,2,3,4-tetrahydroisoquinolines.

In the above formula (I) preferably $R_1$ is hydrogen, OH, $NH_2$, amino($C_1$-$C_3$), amino($C_1$-$C_3$)dialkyl, $CH_2OH$, $COOCH_3$, $OCOOCH_3$, methyl, Et and the like. Most preferably $R_1$ is hydrogen or methyl;

Preferably $R_2$ is (when $R_3$,$R_4$ forms a carbonyl group) Me, Et or $NH_2$, Particularly preferred example of $R_2$ is Me (methyl);

Preferably $R_2$ is (when $R_3$=$R_4$=H) Me, Et, CN, CHO, $COCH_3$ or $COOCH_3$;

Preferably $R_7$ is $OCHF_2$, OMe, $OCH_2CF_3$ or OEt;

Preferably $R_8$ is hydrogen, OH, Me, OMe, halogen or OX; particularly preferably $R_8$ is hydrogen, OH, OMe or OX and $R_7$ is $OCHF_2$, OMe, $OCH_2CF_3$ or OEt. The most preferred substituent pattern for $R_8$ and $R_7$ is $R_8$=hydrogen, OH or OX and $R_7$=$OCHF_2$, $OCH_2CF_3$, OMe or OEt.

$R_9$ designates hydrogen, ($C_1$-$C_6$) alkyl, ($C_1$-$C_6$)alkoxy, ($C_1$-$C_3$)alkyl-$R_{10}$, In the present invention, $R_{10}$ designates at least one (one, two or more) OMe, OEt, OPr, OIsopropyl, OH, CN, $NH_2$, ester groups with ($C_1$-$C_3$)alkyl, carbonate groups with ($C_1$-$C_3$)alkyl.

In formula (I) the substituent on the 4-position may be a phenyl substituent (U=$CR_2$'; V=$CR_4$'; W=$CR_6$'), a 4-pyridyl substituent (U=$CR_2$'; V=N; W=$CR_6$'), a 2-pyridyl substituent (V=$CR_4$'; U=N, W=$CR_6$', or U=$CR_2$', W=N), a 2-pyrimidyl substituent (U, W=N; V=$CR_4$'), a 4-pyrimidyl substituent (V=N; U=CR$_2$', W=N, or U=N, W=CR$_6$'), or a triazinyl substituent (U, V, W=N).

A preferred substitution pattern on said substituent on the 4-position is R$_3$', R$_5$'=each independently chloro, bromo, Me, OMe or OCHF$_2$. Here in one more preferred embodiment R$_3$' and R$_5$' are identical, i.e. they are both chloro, both bromo, both Me, both OMe or both OCHF$_2$; in another preferred embodiment R$_3$' is chloro or bromo, and R$_5$' is OMe. Most preferably both R$_3$' and R$_5$' are chloro, bromo or OCHF$_2$. When the 4-substituent is phenyl then R$_2$' and R$_6$' are preferably hydrogen. R$_4$' then is preferably hydrogen, chloro, bromo, Me, OMe, OCHF$_2$, or OX. Three most preferred substitution patterns on the phenyl as the 4-substituent are a) R$_2$', R$_6$'=hydrogen, R$_3$', R$_4$', R$_5$'=OMe; b) R$_2$', R$_6$'=hydrogen, R$_3$'=chloro, R$_4$', R$_5$'=OMe; and c) R$_2$', R$_6$'=hydrogen, R$_4$'=hydrogen or OX and R$_3$' and R$_5$'=both chloro, both bromo or both OCHF$_2$. Due to the rotational freedom of the phenyl, in b) the definitions for R$_3$' and R$_5$' are interchangeable.

The alkyl residue in the (C$_1$-C$_4$)alkyl or (C$_1$-C$_4$)alkoxy, as used in the substituent definitions of formula (I), may be branched, unbranched or cyclic and may contain double or triple bonds. It is e.g. methyl, ethyl, n-propyl, n-butyl, isopropyl, sec-butyl, t-butyl, cyclopropyl, cyclobutyl, ethenyl or prop-2-enyl, but-1-enyl, but-2-enyl, but-3-enyl or propargyl. Preferably it is methyl, ethyl or isopropyl; particularly preferably it is methyl.

The alkyl residue in the (C$_1$-C$_6$)alkyl or (C$_1$-C$_6$)alkoxy may be unbranched, branched or cyclic and may contain double or triple bonds. Examples of unbranched alkyls are methyl, ethyl, n-propyl, n-butyl, n-pentyl and n-hexyl. Examples of branched alkyl are isopropyl, sec-butyl, t-butyl, (1,1-diethyl)methyl, (1-propyl-1-methyl)methyl, (1-isopropyl-1-methyl)methyl, (1,1-dimethyl-1-ethyl)methyl, (1-t-butyl)methyl, (1-propyl-1-ethyl)methyl, (1-isopropyl-1-ethyl)methyl, (1,1-diethyl-1-methyl)methyl and (1-t-butyl-1-methyl)methyl. Examples of the cyclic alkyl are cyclopropyl, cyclobutyl, cyclopentyl, cyclohexyl or (2- or 3-methyl)cyclopentyl. Examples of unsaturated alkyls are ethenyl, prop-2-enyl, prop-3-enyl, but-1-enyl, but-2-enyl, but-3-enyl, pent-1-enyl, pent-2-enyl, pent-3-enyl, pent-4-enyl, penta-1,3-dienyl, penta-1,4-dienyl, penta-2,4-dienyl or propargyl.

The term "halogen" means in the context of the present application fluoro, chloro or bromo.

In the context of the present application the term "IGF-1 receptor" encompasses human IGF-1 receptor, the amino acid sequence of which is known [see e.g. T. E. Adams et al. Cellular and Molecular Life Sciences 2000, 57, p. 1050-1093], but it also encompasses other IGF-1R, such as IGF-1R of mammals in general.

According to the present invention, pharmaceutically acceptable salts are produced from acidic inorganic or organic compounds, or alkaline inorganic or organic compounds.

As used herein, the phrase "pharmaceutically acceptable salt" refers to a salt that retains the biological effectiveness of the free acids and bases of a specified compound and that is not biologically or otherwise undesirable. The pharmaceutically acceptable salts of the compounds of formula (I) are acid addition salts with pharmaceutically acceptable acids, which are possible in the case where at least one of U, V and W is nitrogen, and when the group X contains a basic nitrogen atom.

A desired salt may be prepared by any suitable method known in the art, including treatment of the free base with an inorganic acid, such as hydrochloric acid, hydrobromic acid, sulphuric acid, nitric acid, phosphoric acid, and the like, or with an organic acid, such as formic acid, acetic acid, maleic acid, succinic acid, mandelic acid, maleic acid, fumaric acid, malonic acid, pyruvic acid, oxalic acid, glycolic acid, salicylic acid; a pyranosidyl acid, such as glucuronic acid or galacturonic acid; an alpha-hydroxy acid, such as citric acid or tartaric acid; an amino acid, such as aspartic acid or glutamic acid; an aromatic acid, such as benzoic acid or cinnamic acid; a sulfonic acid, such as methanesulfonic acid, p-toluenesulfonic acid or ethanesulfonic acid; or the like.

In the present invention the preferred ammonium salts are derived from hydrochloric, hydrobromic, methanesulfonic, acetic, propionic, benzoic, citric, tartaric, malic, maleic, fumaric, lactic, nitric, and phosphoric or succinic acid.

Generally, the salts are prepared by reacting the free base with stoichiometric amounts or with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, symmetrical or asymmetrical ethers containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt from the mixture, or it can be precipitated by the addition of a solvent in which the salt is insoluble and recovered there from.

Examples of suitable inorganic and organic solvents for performing the various reactions include any inorganic or organic solvent that does not adversely affect the reactants or the resulting product, including halogenated solvents such as methylene chloride, chloroform, ether solvents such as diethyl ether, and other solvents such as tetrahydrofuran, dioxane, diglyme, cyclooctane, benzene or toluene, heptane, cyclohexane, aliphatic as well as cycloaliphatic and aromatic hydrocarbon solvents, water, acidified aqueous solutions, mixed organic and inorganic solutions, ethyl acetate, propyl acetate and mixtures thereof.

Also encompassed by the present invention are salts formed from acidic prodrugs, such as phosphates, and alkaline inorganic or organic compounds. Preferred inorganic cations comprised in the salts are lithium, sodium, potassium, rubidium, ammonium, calcium, magnesium, zinc and manganese. Production of phosphate salts are described in e.g. G. R. Pettit et al. *Anti-Cancer Drug Design* 16 (2001) 185-193.

Preferred salts also include those formed from acidic pro-drugs and organic amines, including, but not limited to, imidazole and morpholine. Alkaline amino acid salts may also be used. The term "amino acids" designates, according to the invention, in particular the [alpha]-amino acids occurring in nature, but moreover also includes their homologues, isomers and derivatives. Enantiomers can be mentioned as an example of isomers. Derivatives can be, for example, amino acids provided with protective groups. Preferred alkaline amino acid are arginine, ornithine, diaminobutyric acid, lysine or hydroxy lysine and especially L-arginine, L-lysine or L-hydroxy lysine; an alkaline dipeptide or a pharmaceutically acceptable alkaline amino acid derivate.

The present invention also relates to pro-drugs of a compound of formula I that in vivo convert to the compound of formula I as such. Any reference to a compound of formula I is therefore to be understood as referring also to the corresponding pro-drug of the compound of formula I, as appropriate.

For the purposes of the present invention, a "pro-drug" is an entity which either comprises an inactive form of an active drug (parent compound) or includes a chemical group which confers preferred characteristics on the drug. In other words, it concerns a composition which has the potential of producing a desired physiological effect on cells, but is initially inert (i.e. does not produce said effect), and only after undergoing some modifications becomes physiologically active and produces said physiological effect on cells. In particular, the derivative of the compound of formula I has a chemically or metabolically degradable group, and becomes pharmaceutically active after biotransformation.

Biotransformation of the prodrug or a salt thereof is carried out under physiological conditions (in vivo) and is a result of a reaction with an enzyme, or a body fluid such as gastric acid, blood etc., thus undergoing an enzymatic oxidation, reduction, hydrolysis etc. or a chemical hydrolysis convert into the active parent compound of formula I.

As used herein, the terms "parent compounds" or "active parent compounds" or "active drugs" are used interchangeably herein to designate the compounds of formula I according to the present invention.

The term "physiological effect" concerns any effect a drug may have on cells, in order to improve the health of the subject administered with the drug. The effect is produced in order to treat, prevent a disease, a defect or pathological condition or to alleviate some of the manifestations of a disease, defect or pathological condition.

In the present invention, OX designates a group capable of conferring the prodrug property and wherein an OX group may be present in either $R_8$ or $R_4'$. Alternatively, OX groups may be present in both $R_8$ and $R_4'$ (when V designates $CR_4'$).

Preferably, —OX groups ($R_8$ and/or $R_8'$) designate phosphate derivatives, ester derivatives, carbonate derivatives (acyloxy derivatives of the parent compounds) and/or linked poly(ethylene glycol) derivatives as described below. Any other suitable derivatives known by those skilled in the art and considered as equivalents may also be used in the scope of the present invention.

When the compounds of formula I possess a hydroxyl group, a carbonate derivative, prepared by reacting the compounds of formula I with a suitable alkyl- or arylchloroformate, are exemplified as prodrugs. Particularly preferred acyloxy derivatives as prodrugs are —OCOOCH$_3$— OCOOC$_2$H$_5$, —OCOOPropyl, —OCOOIsopropyl, —OCOOBu, —OCOO(m-COONa-Ph), —OCOOCH$_2$CH$_2$COONa, —OCOOCH$_2$CH$_2$N(CH$_3$)$_2$, and the like.

Examples of ester derivatives are formates, acetates, benzoates (e.g. OCO(m-COONa-Ph), dimethylglycine esters, aminoalkyl esters, carboxyalkyl esters, esters with amino acids, and the like.

Most preferably, OX groups designate phosphate derivatives.

The invention also encompasses chemical modifications of the compounds of formula I to prolong their circulating lifetimes. Examples of suitable poly(ethylene glycol) derivatives that possess this property are described in e.g. US 2005171328 (NEKTAR THERAPEUTICS AL CORP) or U.S. Pat. No. 6,713,454 (NOBEX CORP). Since the compounds of formula I are fairly lipophilic, the PEG-oligomer/polymer also increases the hydrophilicity of the pro-drugs and thereby their aqueous solubility.

The selection method and the process method of an appropriate prodrug derivative are described in the literature such as *Design of Prodrugs, Elsevier, Amsterdam* 1985; G. R. Pettit et al. *Anti-Cancer Drug Design* 16 (2001) 185-193.

The compounds (I) of the present invention can be prepared using the methods described below, with reference to Schemes 1, 2 3 and 4. Preferably, as depicted in schemes 1 and 2, the compounds (I) of the present invention are synthesized by reacting an appropriately substituted benzylamine (III) with an appropriately substituted and protected mandelic acid (VII) to give the amides (VIII). Treatment of the amides (VIII) with a strong Lewis acid, such as trifluoroacetic acid, generates the compounds (I) ($R_3,R_4$=carbonyl group). An alternative method for the production of compounds (I) is depicted in Schemes 3 and 4. The latter method is especially suitable in cases where the 4-aryl group contains two or more electron withdrawal substituents, or when $R_4'$=H.

Methods for the production of some derivatives of 4-aryl-1,4-dihydro-3(2H)-isoquinolines have been described previously: [D. J. Hart, et al. J. Am. Chem. Soc. 100 (1978) 1548-1557; S. V. Kessar, et al. J. C. S. Chem. Comm. (1989) 1074-1075; A. P. Venkov, et al. Synthesis (1982) 486-487; O. S. Petrov, et al. Synthesis (1987) 637-638; A. P. Venkov, et al., Synthesis (1991) 476-478; N. Coskun, et al. Synthetic Communications 23 (1993) 1393-1402; J. Toda, et al. ARKIVOC (2000, Vol. 1, Part 2) 165-180; T. Honda, et al. J. Org. Lett. 3 (2001) 631-633].

Reduction of compounds I ($R_3,R_4$=carbonyl group) with e.g. lithium aluminium hydride [described by J. Toda et al. ARKIVOC (2000, Vol. 1, Part 2) 165-180] or sodium dihydrido-bis(2-methoxy-ethoxy)aluminate (Red-Al), give derivatives of 4-aryl-1,2,3,4-tetrahydroisoquinoline (I, $R_3$=$R_4$=H).

The amines (III) may be prepared from appropriately substituted benzaldehydes (II) or benzophenones (II) by techniques known in the art. For the production of the amines (III) reference is made to U. Holzgrabe [Arch. Pharm. Weinheim 320 (1987) 647-654], A. P. Venkov et al. [Synthesis, 1991, 476-478] and H. J. Kumpaty et al. [Synthetic Communications 33 (2003) 1411-1416].

Appropriately substituted benzaldehydes and benzophenones are known or may easily be synthesized by using standard procedures. It will be appreciated by those skilled in the art that in processes of the present invention certain functional groups such as hydroxyl groups in the starting reagents or intermediate compounds may need to be protected by protecting groups. Thus, the preparation of the compounds (I) may involve the addition and removal of one or more protecting groups. The protection and deprotection of functional groups is described in "Protective Groups in Organic Chemistry", edited by J. W. F. McOmie, Plenum Press (1973) and "Protective Groups in Organic Synthesis", 2$^{nd}$ edition, T. W. Greene and P. G. M. Wuts, Wiley-Interscience (1991).

Appropriately substituted benzophenones are easily available from the corresponding benzaldehydes. Reaction of a substituted benzaldehyde with e.g. alkyllithium or an alkyl Grignard reagent gives a 1-aryl-1-hydroxyalkane, which by oxidation generates the desired benzophenone derivative.

Suitable protecting groups for aromatic hydroxyl groups in the present invention are e.g. benzyl and isopropyl groups. Removal of the benzyl group and the isopropyl group is easily achieved by catalytic hydrogenation (catalyst Pd/carbon) and treatment with BCl$_3$, respectively. Another reagent is trimethyl-iodosilane, which is especially useful in the presence of difluoromethoxy groups.

The appropriately substituted benzaldehydes (II) of Scheme 1 are either commercially available or known from the literature. Some examples of known benzaldehydes (II) that may be used for synthesizing some preferred compounds (I) are the following:

| benzaldehydes (II) | CAS reg. no. |
|---|---|
| 3-methoxybenzaldehyde | 591-31-1 |
| 2-fluoro-3-methoxybenzaldehyde | 103438-88-6 |
| 2-chloro-3-methoxybenzaldehyde | 54881-49-1 |
| 2-bromo-3-methoxybenzaldehyde | 10401-18-0 |
| 2-hydroxy-3-methoxybenzaldehyde | 148-53-8 |
| 3-ethoxybenzaldehyde | 22924-15-8 |
| 2-chloro-3-ethoxybenzaldehyde | 99586-82-0 |
| 3-ethoxy-2-hydroxybenzaldehyde | 492-88-6 |
| 2-chloro-3-methylbenzaldehyde | 61563-28-8 |
| 2-bromo-3-methylbenzaldehyde | 109179-31-9 |
| 3-isopropoxybenzaldehyde | 75792-33-5 |
| 2-hydroxy-3-propyloxybenzaldehyde | 222031-84-7 |
| 3-butyloxy-2-hydroxybenzaldehyde | 91849-57-9 |
| 2-hydroxy-3-isobutyloxybenzaldehyde | 222031-85-8 |
| 2-hydroxy-3-isopropoxybenzaldehyde | 222031-87-0 |
| 3-methylbenzaldehyde | 620-23-5 |
| 2-hydroxy-3-methylbenzaldehyde | 824-42-0 |
| 2,3-dimethoxybenzaldehyde | 86-51-1 |
| 2,3-diethoxybenzaldehyde | 24454-82-8 |
| 2-ethoxy-3-methoxybenzaldehyde | 66799-97-1 |
| 3-ethoxy-2-methoxybenzaldehyde | 75792-34-6 |
| 3-isopropoxy-2-methoxybenzaldehyde | 218903-24-3 |
| 2-methoxy-3-methylbenzaldehyde | 67639-61-6 |
| 2-ethoxy-3-methylbenzaldehyde | 532965-62-1 |
| 3-methoxy-2-methylbenzaldehyde | 56724-03-9 |
| 3-hydroxy-2-ethylbenzaldehyde | 532966-36-2 |
| 3-methoxy-2-propylbenzaldehyde | 97582-12-2 |
| 2-isopropyl-3-methoxybenzaldehyde | 93351-17-8 |
| 2-butyl-3-methoxybenzaldehyde | 151038-64-1 |
| 2-(1,1-dimethylethyl)-3-methoxybenzaldehyde | 151038-66-3 |
| 3,4-methylenedioxybenzaldehyde | 120-57-0 |
| 3,4-ethylenedioxybenzaldehyde | 29668-44-8 |
| 3-(trifluoromethoxy)benzaldehyde | 52771-21-8 |
| 3-hydroxy-2-methoxybenzaldehyde | 66495-88-3 |
| 3-hydroxy-2-ethoxybenzaldehyde | 182067-51-2 |
| 3-hydroxy-2-propoxybenzaldehyde | 508202-83-3 |
| 3-(methylthio)benzaldehyde | 73771-35-4 |
| 3-(ethylthio)benzaldehyde | 87425-00-1 |
| 3-bromo-2-fluorobenzyldehyde | 149947-15-9 |
| 2-fluoro-3-hydroxybenzaldehyde | 103438-86-4 |
| 2-chloro-3-hydroxybenzaldehyde | 56962-10-8 |
| 2-bromo-3-hydroxybenzaldehyde | 196081-71-7 |
| 3-hydroxybenzaldehyde | 100-83-4 |
| 3-hydroxy-2-methylbenzaldehyde | 90111-15-2 |
| 3-hydroxy-2-propylbenzaldehyde | 532966-38-4 |
| 3-hydroxy-2-isopropylbenzaldehyde | 532966-40-8 |
| 2-butyl-3-hydroxybenzaldehyde | 532966-42-0 |
| 2-(1,1-dimethylethyl)-3-hydroxybenzaldehyde | 532966-46-4 |
| 3-hydroxy-2-(1-methylpropyl)benzaldehyde | 532966-44-2 |
| 2-hydroxy-3-trifluoromethoxybenzaldehyde | 497959-31-6 |
| 2-hydroxy-3-(methylthio)benzaldehyde | 67868-82-0 |
| 3-benzyloxy-2-hydroxybenzaldehyde | 86734-59-0 |

Scheme 1

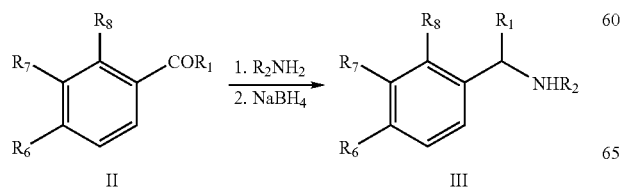

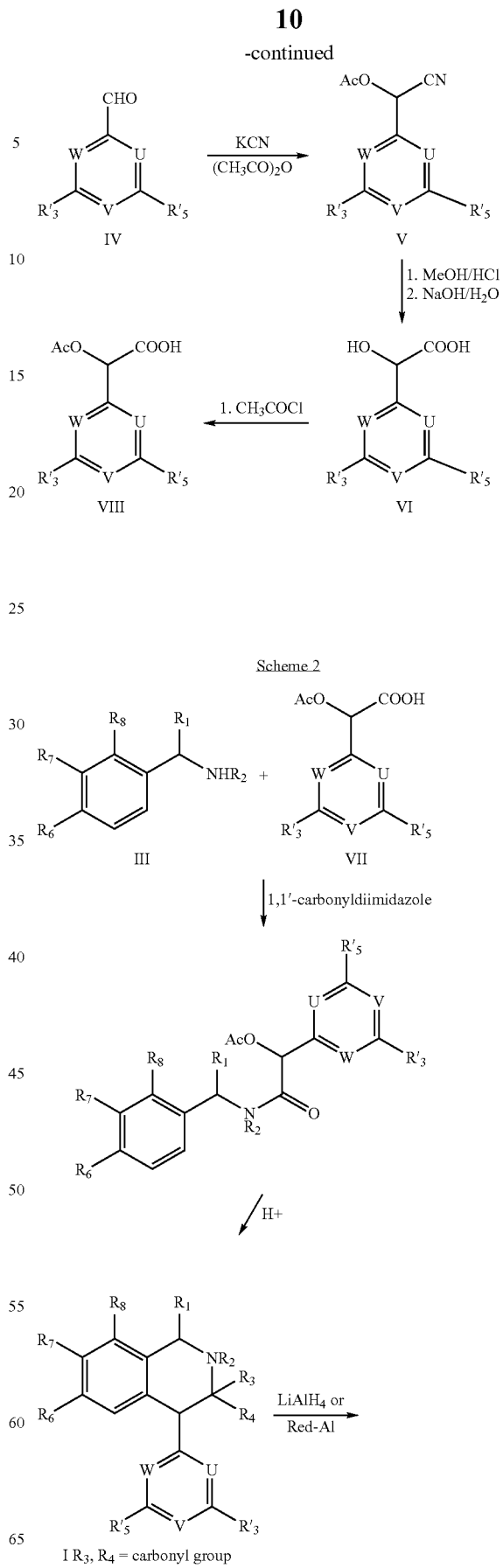

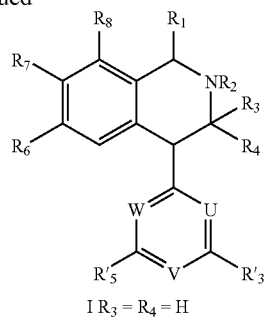
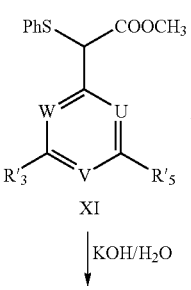
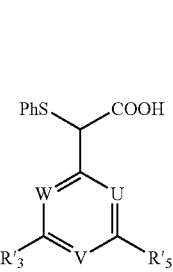
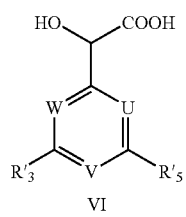
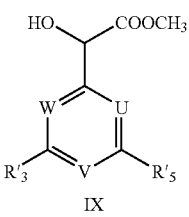
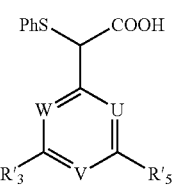
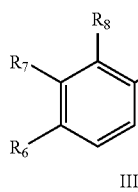
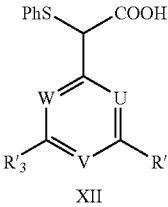
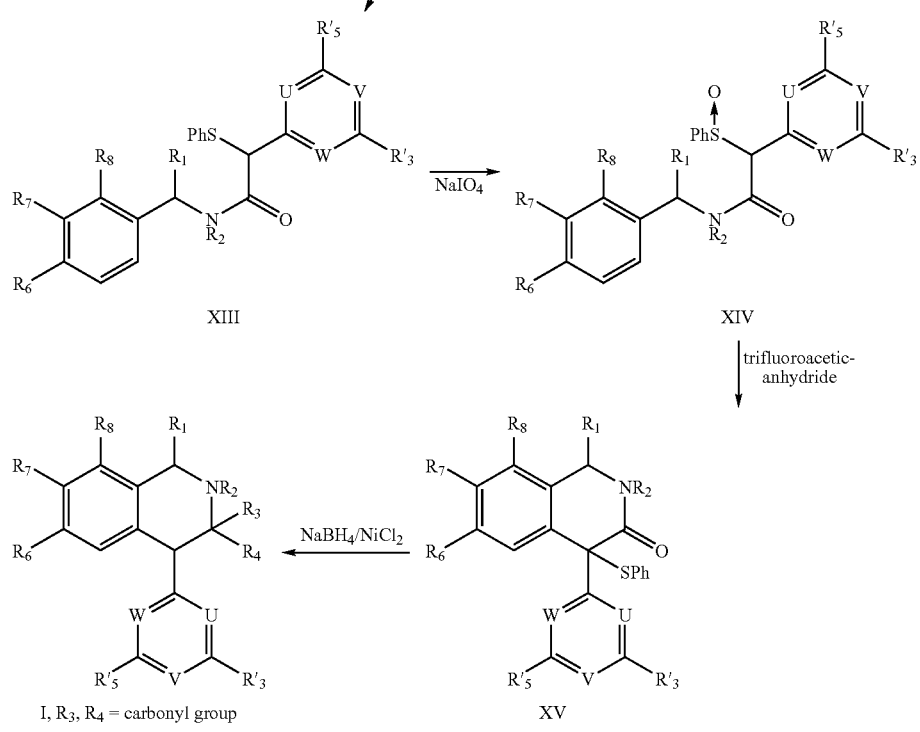

2-($C_1$-$C_4$)alkyl-3-($C_1$-$C_4$)alkoxybenzaldehydes [i.e. with $R_8$=($C_1$-$C_4$)alkyl, $R_7$=($C_1$-$C_4$)alkoxy] may be synthesized from 2-($C_1$-$C_4$)alkyl-3-hydroxy-benzaldehydes by Williamson etherification with a corresponding ($C_1$-$C_4$)alkyl bromide. 2-($C_1$-$C_4$)alkyl-3-tri-fluoromethoxybenzaldehydes [i.e. with $R_8$=($C_1$-$C_4$)alkyl, $R_7$=$OCF_3$], may be synthesized from the corresponding 3-alkylxanthates by treatment with 1,3-dibromo-5,5-dimethylhydantoin and HF/pyridine [Raab, C. E. et al. *J. Labelled Cpd Radiopharm* 44 (2001) 815-829, and References cited therein]. Trifluoroethoxy groups are conveniently introduced by treatment of a suitable phenoxide ion with 2,2,2-trifluoroethyl methansulphonate in e.g. DMF at 60° C. to 140° C. [Camps, F. et al. *Synthesis* (1980) 727-728]. Difluoromethoxy groups may be introduced by reacting a suitable phenol with a metal carbonate and methyl chlorodifluoroacetate in DMF at 60° C. to 120° C. [see e.g. patent publication EP0812308B1].

2-($C_1$-$C_4$)alkoxy-3-($C_1$-$C_4$)alkoxybenzaldehydes [i.e. with $R_8$=($C_1$-$C_4$)alkoxy, $R_7$=($C_1$-$C_4$)alkoxy] and 2-($C_1$-$C_4$)alkoxy-3-trifluoromethoxybenzaldehydes [i.e. with $R_8$=($C_1$-$C_4$)alkoxy, $R_7$=$OCF_3$], respectively, may be synthesized from 2-($C_1$-$C_4$)alkoxy-3-hydroxy-benzaldehydes by Williamson etherification with a corresponding ($C_1$-$C_4$)alkyl bromide and by applying the "xanthate reaction" as described above, respectively. Alternatively all these compounds are available from 3-benzyloxy-2-hydroxy-benzaldehyde by etherification, followed by debenzylation and etherification of the 3-hydroxy group.

2-($C_1$-$C_4$)alkyl-3-methylthio-benzaldehydes [i.e. with $R_8$=($C_1$-$C_4$)alkyl, $R_7$=SMe] and 2-($C_1$-$C_4$)alkyl-3-ethylthiobenzaldehydes [i.e. with $R_8$=($C_1$-$C_4$)alkyl, $R_7$=Set], respectively, may be synthesized from 2-($C_1$-$C_4$)alkyl-3-bromobenzaldehyde diethyl acetals by reacting its Grignard reagent with dimethyl sulphide or diethyl sulphide, respectively (for a similar reaction see M. Euerby et al., Synthetic Communications 11 (1981), 849-851).

2-($C_1$-$C_4$)alkoxy-3-methylthiobenzaldehydes (i.e. with $R_8$=($C_1$-$C_4$)alkoxy, $R_7$=SMe) and 2-($C_1$-$C_4$)alkoxy-3-ethylthiobenzaldehydes (i.e. with $R_8$=($C_1$-$C_4$)alkOXy, $R_7$=Set), respectively, may be synthesized from 2-($C_1$-$C_4$) alkoxy-3-bromobenzaldehydes by reacting its Grignard reagent with dimethyl sulphide or diethyl sulphide, respectively (for a similar reaction see M. Euerby et al., Synthetic Communications 11 (1981), 849-851). Another route to these starting materials is by etherification of 2-hydroxy-3-(methylthio)benzaldehyde or 2-hydroxy-3-(ethylthio)benzaldehyde (A. Makoto et al. Bull. Chem. Soc. Jpn. 51 (1978) 2435-2436

The appropriately substituted mandelic acids (VI) of Scheme 1 are either commercially available, known from the literature or easily synthesized from appropriately substituted benzaldehydes (V) or benzoic acids in accordance with procedures outlined in the General Methods below, or by other techniques known by those skilled in the art. Enantiomeric pure substituted mandelic acids can be produced by resolution of the corresponding racemates by crystallization of their salts with optically active amines [Colon, D. F. Et al. J. Org. Chem. 56 (1991) 2322-2326], or by enzymatic resolution [Campbell, R. F. et al. Tetrahedron Letters 44 (2003) 5477-5481].

Some examples of known mandelic acids (VI) that may be used for synthesizing some preferred compounds (I) are listed below. Included are also some benzaldehydes (V) and benzoic acids that may serve as starting materials for the production of mandelic acids (V) suitable for the production of some preferred compounds (I).

|  | CAS No. |
|---|---|
| mandelic acids (VI) | |
| 3,4,5-trimethoxymandelic acid | 13212-99-2 |
| 3,5-dimethoxymandelic acid | 187752-49-4 |
| 3,5-dichloromandelic acid | 35599-94-1 |
| 3,5-bis(trifluoromethyl)mandelic acid | 228107-82-2 |
| 3,5-dimethylmandelic acid | 187752-85-8 |
| 3,5-difluoromandelic acid | 132741-31-2 |
| 3,4,5-trimethylmandelic acid | 5766-33-6 |
| 3,5-dimethyl-4-methoxymandelic acid | 147166-58-3 |
| benzaldehydes (V) | |
| 3-bromo-5-methoxybenzaldehyde | 262450-65-7 |
| 3,5-dibromobenzaldehyde | 56990-02-4 |
| 3,4,5-trifluorobenzaldehyde | 132123-54-7 |
| 3,5-dihydroxy-4-methoxybenzaldehyde | 29865-85-8 |
| 3,4-dihydroxy-5-methoxybenzaldehyde | 3934-87-0 |
| 3-chloro-4-hydroxy-5-methoxybenzaldehyde | 19463-48-0 |
| 3-bromo-5-isopropoxy-4-methoxybenzaldehyde | 400070-31-7 |
| 3,5-dibromo-4-isopropoxybenzaldehyde | 486996-44-5 |
| 3-chloro-4-isopropoxy-5-methoxybenzaldehyde | 428847-03-4 |
| 3-hydroxy-4,5-dimethoxybenzaldehyde | 29865-90-5 |
| 3-fluoro-5-(trifluoromethyl)benzaldehyde | 188815-30-7 |
| 3-chloro-5-methylbenzaldehyde | 103426-20-6 |
| 3,4,5-trichlorobenzaldehyde | 56961-76-3 |
| 3-bromo-5-chlorobenzaldehyde | 188813-05-0 |
| 4-bromo-3,5-dimethoxybenzaldehyde | 31558-40-4 |
| 4-chloro-3,5-dimethoxybenzaldehyde | 56518-48-0 |
| 3,5-dimethoxy-4-methylbenzaldehyde | 1011-27-4 |
| 3,5-dibromo-4-methoxybenzaldehyde | 108940-96-1 |
| 3,5-dichloro-4-methoxybenzaldehyde | 41727-58-6 |
| 3-chloro-4,5-dimethoxybenzaldehyde | 18268-68-3 |
| 3-methoxy-5-methylbenzaldehyde | 90674-26-3 |
| 3,5-difluoro-4-methoxybenzaldehyde | 654-11-5 |
| 3,5-dimethoxy-4-isopropoxybenzaldehyde | 2702-54-7 |
| 3-bromo-4,5-dimethoxybenzaldehyde | 6948-30-7 |
| 3,4-dichloro-5-methoxybenzaldehyde | 63001-43-4 |
| 3,5-diethylbenzaldehyde | 81698-95-5 |
| 3,5-dibromo-4-fluorobenzaldehyde | 477535-39-0 |
| 2,3,5-trimethoxybenzaldehyde | 5556-84-3 |
| 5-bromo-2,3-dimethoxybenzaldehyde | 71295-21-1 |
| 3-chloro-5-methoxybenzaldehyde | 164650-68-4 |
| 3,5-dimethoxy-4-hydroxybenzaldehyde | 134-96-3 |
| 3,5-dichloro-4-hydroxybenzaldehyde | 2314-36-5 |
| 3-bromo-5-chloro-4-hydroxybenzaldehyde | 1849-76-9 |
| 3-chloro-4-hydroxy-5-methoxybenzaldehyde | 107356-10-5 |
| 3-bromo-4-hydroxy-5-methoxybenzaldehyde | 2973-76-4 |
| Benzoic acids | |
| 3,5-dichloro-4-isopropoxybenzoic acid | 41490-10-2 |
| 3,5-difluoro-4-methylbenzoic acid | 103877-76-5 |
| 3,5-dichloro-4-methylbenzoic acid | 39652-34-1 |
| 3,5-diethyl-4-methoxybenzoic acid | 250609-63-3 |

Some examples of suitable starting materials for the production of pyridine-, pyrimidine- and triazine-α-hydroxyacetic acids (VI) are the following known compounds:

|  | CAS No. |
|---|---|
| aldehydes (V) | |
| 4,6-dimethoxypyrimidine-2-carboxaldehyde | 125966-89-4 |
| 2,6-dichloro-4-pyridinecarboxaldehyde | 113293-70-2 |
| 2-chloro-6-methoxy-4-pyridinecarboxaldehyde | 329794-31-2 |
| 4,6-dichloro-2-pyridinecarboxaldehyde | 132683-62-6 |
| 4,6-dimethoxy-2-pyridinecarboxaldehyde | 65873-47-4 |
| 4,6-dimethoxy-1,3,5-triazine-2-carboxaldehyde | 98141-06-1 |
| Starting materials for production of aldehydes (V) | |
| 2,6-dichloro-4-pyrimidinecarboxylic acid | 16492-28-7 |
| 4,6-dichloro-1,3,5-triazine-2-carboxamide | 583630-76-6 |
| 4,6-dimethyl-1,3,5-triazine-2-ethylcarboxylate | 829-73-2 |

The transformation of carboxylic acids, amides and ethyl esters into their corresponding aldehydes are routine procedures known by those skilled in the art.

The compounds of the present invention contain at least one chiral centre and therefore may exist in different enantiomeric forms. Although particularly preferred compounds (I) are enantiomerically pure the scope of the present invention is intended to cover all enantiomers per se, as well as mixtures of them in any ratio, such as racemic mixtures.

Compounds (I) of the present invention may be obtained in their enantiomerically pure forms by crystallization of their addition salts with chiral acids [see e.g. D. L. Minor et al. J. Med. Chem. 37 (1994) 4317-4328; U.S. Pat. No. 4,349,472], or alternatively, may be isolated by preparative HPLC using commercially available chiral phases. Other routes to the pure enantiomers of the products of the present invention are the use of asymmetric synthesis [N. Philippe et al. Tetrahedron 59 (2003) 8049-8056] or by resolution of chiral diastereometric derivatives thereof, as known by those skilled in the art.

The compounds of formula (I), their pharmaceutically acceptable salts and pro-drugs thereof, where applicable, may be administered in the form of a pharmaceutical composition in which they are in association with a pharmaceutically acceptable adjuvant, diluent or carrier, in order to prevent or treat any disease in which inhibition of the IGF-1 receptor would be considered beneficial by the skilled person. The present invention also provides a pharmaceutical composition comprising a compound of formula (I), or a pharmaceutically acceptable salt thereof, as hereinbefore defined, in association with a pharmaceutically acceptable adjuvant, diluent or carrier. As to the appropriate excipients, diluents and adjuvants, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002.

The compounds of formula (I) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in microemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the compounds of formula (I), which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma]ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The compounds (I) of the examples of the present invention have IC50 activities in intact cell systems ranging from 8 microgram/ml to 3 nanogram/ml. Due to the large difference in activities, the pharmaceutical compositions of the invention will preferably comprise from 0.001 to 50% by weight of compound (I).

The daily dose of compounds (I) will necessarily be varied depending upon the host treated, the particular route of administration, and the severity and kind of the illness being treated. Accordingly the optimum dosage may be determined by the practitioner who is treating any particular patient.

The pharmaceutical compositions of the invention may be formulated as creams, gels, solutions, ointments, suspensions or plasters etc. when intended for topical administration; for administration by inhalation, e.g. as aerosols or dry powders; for oral administration, e.g. in the form of tablets, capsules, gels, syrups, suspensions, solutions, powders or granules; for rectal or vaginal administration e.g. as suppositories; or for parenteral injection (including intravenous, subcutaneous, intramuscular, intravascular, or infusion) as a sterile solution, suspension or emulsion.

The compounds of the present invention were found to down-regulate or inhibit the expression or function of the human IGF-1 receptor, without inhibiting the structurally closely related insulin receptor. They were found to promote apoptosis of malignant cells and to interfere with cell division by blocking the cells in the prophase of the mitotic cycle. The compounds (I) are useful for the prevention and/or treatment of diseases of unregulated IGF-1R expression, including cell proliferate diseases such as cancer, atherosclerosis, restinosis, inflammatory diseases e.g. psoriasis, autoimmune diseases e.g. rheumatoid arthritis, and transplant rejection.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

"Mammal" for purposes of treatment refers to any animal classified as a mammal, including humans, domestic and farm animals or pet animals, such as dogs, horses, cats, cows, monkeys etc. Preferably, the mammal is human.

The term "therapeutically effective amount" refers to an amount of a drug effective to treat a disease or disorder in a mammal. In the case of cancer, the therapeutically effective amount of the drug may reduce the number of cancer cells; reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; and/or relieve to some extent one or more of the symptoms associated with the cancer. To the extent the drug may prevent growth and/or kill existing cancer cells, it may be cytostatic and/or cytotoxic. The phrase "therapeutically effective amount" is used herein to mean an amount sufficient to prevent, or preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells or tumour, or other feature of pathology.

The terms "cancer" and "cancerous" refer to or describe the physiological condition in mammals that is typically characterized by unregulated cell growth.

Some examples of cancers in which IGF-1R is unregulated or over expressed and which can be prevented and/or treated by the compounds of formula (I) include, but are not limited to, cancer of the breast, prostate, colon, lung, brain, kidney, pancreas, and melanoma, multiple myeloma, lymphoma and leukemia.

Optionally the compounds (I) may be used against cell proliferate diseases in combination with conventional treatments such as irradiation and/or one or more chemotherapeutic agents such as e.g. Actinomycin, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplati, Pentostatin, Procarbazine, Streptozocin, Taco, Temozolomide, Tioguanine/Thioguanine, Thiotepa, Topotecan, Treosulfan, Vinblastine, Vincristine, Vindesine or Vinorelbine.

When a chemotherapeutic agent is used in combination with the compounds of formula (I), then this may be used in the form of a medicament containing a combination of these two agents, for simultaneous administration, or they may be used in the form of separate dosage forms, each containing one of the agents, and in the latter case the individual dosage forms may be used e.g. sequentially, i.e. one dosage form with the compound (I), followed by a dosage form containing the chemotherapeutic agent (or vice versa). This embodiment of two separate dosage forms may be conceived and provided in the form of a kit.

Generally, the Kit comprises a container and a label or package insert on or associated with the container. Suitable containers include, for example, bottles, vials, syringes, etc. The containers may be formed from a variety of materials such as glass or plastic. The container holds the compound's composition or the pro-drug composition or pharmaceutically acceptable salts thereof that are effective for treating the condition and may have a sterile access port (for example the container may be an intravenous solution bag or a vial having a stopper pierceable by a hypodermic injection needle). The label or package insert indicates that the composition is used for treating the condition of choice, such as cancer.

In addition to their use in therapeutic medicine, the compounds (I) and their pharmaceutically acceptable salts are also useful as pharmacological tools in the development and standardization of in vitro and in vivo test systems for the evaluation of the effects of inhibitors of cell cycle activity in laboratory animals such as cats, dogs, rabbits, monkeys, rats and mice, as part of the search for new therapeutic agents.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Products described in the Examples have satisfactory proton nuclear magnetic resonance spectra and/or mass spectral data. Melting points are uncorrected. The substances described in the examples are racemates, unless marked with (+) or (−), which denotes the dextrorotatory enantiomer and levorotatory enantiomer, respectively. Isolation of the pure enantiomers was accomplished by chromatography on a Chiralcel OD-R column (Daicel) using mixtures of acetonitril and water [0.5 mol/l of sodium perchlorate containing 1.1% v/v of a mixture of acetic acid and triethylamine (2 M/1 M)] as eluent, or on, a Chiralcel-OD-I (20 μM) column using mixtures of t-butyl methyl ether and dichloromethane as eluent.

Examples 1 to 18

Syntheses of Compounds (I)

In the examples 1 to 18 the following General Methods were used unless otherwise stated:

1. Production of Amines (III, Scheme 1):

The appropriate amine (0.1 mol) was added to a solution of the appropriate benzaldehyde (II, 0.1 mol) in methanol (300 ml). After stirring at room temperature for 1 hour, the solution was cooled to 0° C. prior to addition of sodium borohydride (0.05 mol) portion wise. The resulting solution was stirred at room temperature for 1 hour, after which it was concentrated to dryness. The residue was partitioned between dichloromethane (300 ml) and an aqueous solution of sodium hydroxide (200 ml, 2M). The dichloromethane phase was separated and extracted with hydrochloric acid (2×200 ml, 2M). The aqueous phase was made alkaline (pH 11-12) and extracted with dichloromethane (2×200 ml). The organic phase was dried (sodium sulphate) and concentrated to dryness, leaving the amine (III), which was used without further purification.

In cases where the starting amine is volatile, the corresponding hydrochloride can also be used together with an equimolar amount of solid sodium hydroxide.

2. Production of aryl-α-hydroxyacetic Acids (VI).

A mixture of potassium cyanide (0.25 mol), triethylbenzylammonium chloride (0.009 mol), water (50 ml) and dichloromethane (50 ml) was cooled to 0° C. To the vigorously stirred mixture, a solution containing the appropriate aldehyde (IV, 0.2 mol) and acetic anhydride (0.2 mol) in dichloromethane (60 ml) was added drop wise at 0° C. during 30 minutes. The stirring was continued at 0° C. for 30 minutes and then at ambient temperature for one hour. The organic phase was separated, dried and concentrated to dryness, leaving crude aryl-α-acetoxyacetonitrile. Crystallization from ethanol-water afforded pure aryl-α-acetoxyacetonitrile (V).

Dry hydrogen chloride (3 mol) was bubbled through a solution of the appropriate aryl-α-acetoxyacetonitrile (0.35 mol) in anhydrous methanol (1000 ml) for 50 minutes at 15° C. After standing at room temperature for two hours, the mixture was concentrated to dryness. The residue was stirred with water (750 ml) for two hours, after which sodium hydroxide (100 g) was added and the stirring continued over night. The mixture was acidified with concentrated hydrochloric acid, saturated with sodium chloride and extracted with ethyl acetate (3×250 ml). The organic phase was dried and concentrated to dryness, leaving crude aryl-α-hydroxyacetic acid (VI), 3. Production of aryl-α-acetyloxyacetic Acids (VII).

The appropriate substituted mandelic acid (0.2 mol) was treated with acetyl chloride (100 ml) at room temperature for three hours. The clear solution was concentrated to dryness under vacuum, and the residual aryl-α-acetyloxyacetic acid was used as such in subsequent reaction, or purified by crystallization from e.g. toluene.

4. Production of Amides (VIII) and (XIII).

A solution of the appropriate aryl-α-acetyloxyacetic acid (VII) or 2-aryl-2-(phenylsulfanyl)acetic acid (XII) (0.02 mol) in dichloromethane (40 ml) was reacted with 1,1'-carbonyldiimidazole (0.021 mol) at room temperature for 30 minutes. The resulting clear solution was reflux for 30 minutes, after which the appropriate amine (0.021 mol) dissolved in dichloromethane (10 ml) was added. The mixture was stirred at room temperature for 2 hours, after which it was washed with aqueous hydrochloric acid (20 ml, 1M) followed by aqueous sodium hydrogen carbonate (20 ml, 0.5 M). The organic phase was dried and concentrated to dryness, leaving crude amide VIII or XIII. Amides VIII and XIII were used in the production of compounds of formula I without further purification.

5. Production of Compounds I from Amides VIII.

A solution of the appropriate amide VIII (0.02 mol) in dichloromethane (60 ml) and trifluoroacetic acid (20 ml) was refluxed for 2 to 6 hours. The mixture was concentrated to dryness, and the residue was crystallized from methanol or ethanol leaving the pure compounds I ($R_3$,$R_4$=carbonyl group).

By appropriate use of the above outlined general synthesis steps 1-5, and methodology described in the "Detailed description of the production of some representative examples", compounds (I) according to the following Table 1 were prepared. Melting points given in the table are uncorrected.

TABLE 1

| Ex. | compound (I) | appearance | crystallization solvent | m.p. ° C. |
|---|---|---|---|---|
| 1 | 2-methyl-4-(3,4,5-trimethoxyphenyl)-7-methoxy-1,4-dihydro-3(2H)-isoquinolinone | white solid | methanol | 170-172 |
| 2 | 2-methyl-4-(3,4,5-trimethoxyphenyl)-6,7-methylenedioxy-1,4-dihydro-3(2H)-isoquinolinone | white solid | methanol | 150-152 |
| 3 | 2-(2-dimethylaminoethyl)-4-(3,4,5-trimethoxyphenyl)-7-methoxy-1,4-dihydro-3(2H)-isoquinolinone hydrochloride | white solid | ethanol/diethyl ether | 112-114 |
| 4 | 2-methyl-4-(3,4,5-trimethoxyphenyl)-7-methyl-1,4-dihydro-3(2H)-isoquinolinone | white solid | methanol | 138-140 |
| 5 | 2-methyl-4-(3,4,5-trimethoxyphenyl)-7,8-dimethoxy-1,4-dihydro-3(2H)-isoquinolinone | white solid | methanol | 102-104 |
| 6 | 2-methyl-4-(3,4,5-trimethoxyphenyl)-8-isopropoxy-7-methoxy-1,4-dihydro-3(2H)-isoquinolinone | white solid | methanol | 128-129 |
| 7 | 2-methyl-4-(3,4,5-trimethoxyphenyl)-7-ethoxy-1,4-dihydro-3(2H)-isoquinolinone | white solid | methanol | 132-134 |
| 8 | 2-methyl-4-(3,4,5-trimethoxyphenyl)-7,8-ethylenedioxy-1,4-dihydro-3(2H)-isoquinolinone | white solid | methanol | 161-163 |
| 9 | 2-methyl-4-(3,4,5-trimethoxyphenyl)-6,7-ethylenedioxy-1,4-dihydro-3(2H)-isoquinolinone | white solid | methanol | 148-149 |
| 10 | 2-methyl-4-(3-chloro-4,5-dimethoxyphenyl)-7-methoxy-1,4-dihydro-3(2H)-isoquinolinone | white solid | methanol | 118-120 |
| 11 | 2-methyl-4-(3,5-dichlorophenyl)-7-methoxy-1,4-dihydro-3(2H)-isoquinolinone | white solid | methanol | 163-165 |
| 12 | 2-amino-4-(3,4,5-trimethoxyphenyl)-7-methoxy-1,4-dihydro-3(2H)-isoquinolinone hydrochloride | white solid | methanol | 164-167 |
| 13 | 2-methyl-4-(3,5-dimethoxyphenyl)-7-methoxy-1,4-dihydro-3(2H)-isoquinolinone | white solid | methanol | 137-139 |
| 14 | 2-ethyl-4-(3,4,5-trimethoxyphenyl)-7-methoxy-1,4-dihydro-3(2H)-isoquinolinone | white solid | methanol | 155-157 |
| 15 | (+)-2-methyl-4-(3,4,5-trimethoxyphenyl)-8-hydroxy-7-methoxy-1,4-dihydro-3(2H)-isoquinolinone | white solid | methanol | 193-196 |
| 16 | 2-methyl-4-(3,4,5-trimethoxyphenyl)-7-methoxy-1,2,3,4-tetrahydroisoquinoline hydrochloride | white solid | methanol | 201-204 |
| 17 | 1,2-dimethyl-4-(3,4,5-trimethoxyphenyl)-7-methoxy-1,4-dihydro-3(2H)-isoquinolinone | | | |
| | Diastereomer I | white solid | diethyl ether | 135-140 |
| | Diastereomer II | amorphous solid | | |
| 18 | 2-cyano-4-(3,4,5-trimethoxyphenyl)-7-methoxy-1,2,3,4-tetrahydroisoquinoline | white solid | methanol | 113-116 |

Detailed Description of the Production of Some Representative Examples

Compound 9: 2-methyl-4-(3,4,5-trimethoxyphenyl)-6,7-ethylenedioxy-1,4-dihydro-3(2H)-isoquinolinone 1. Methylamine hydrochloride (16.5 g) and sodium hydroxide (9.8 g) were added to a solution of 3,4-ethylenedioxybenzaldehyde (40.0 g) in methanol (700 ml). After stirring at room temperature for one hour, the solution was cooled to 0° C. prior to addition of sodium borohydride (4,5 g) portion wise. The resulting solution was stirred at room temperature for one hour, after which it was concentrated to dryness. The residue was partitioned between dichloromethane (500 ml) and an aqueous solution of sodium hydroxide (400 ml, 2M). The dichloromethane phase was separated and extracted with hydrochloric acid (2×300 ml, 2M). The aqueous phase was made alkaline (pH 11-12) and extracted with dichloro-methane (2×300 ml). The organic phase was dried (sodium sulphate) and concentrated to dryness, leaving N-methyl-3,4-ethylenedioxybenzylamine, which was used without further purification.

2. A mixture of potassium cyanide (41.5 g), triethylbenzylammonium chloride (5.23 g), water (130 ml) and dichloromethane (150 ml) was cooled to 0° C. To the vigorously stirred mixture, a solution containing the 3,4,5-trimethoxybenzaldehyde (100.0 g) and acetic anhydride (52.1 g) in dichloromethane (150 ml) was added drop wise at 0° C. during 30 minutes. The stirring was continued at 0° C. for 30 minutes and then at ambient temperature for one hour. The organic phase was separated, dried and concentrated to dryness, leaving crude 3,4,5-trimethoxyphenyl-α-acetoxyacetonitrile. Crystallization from ethanol-water afforded the pure product (104 g), m.p. 65-66° C.

3. Dry hydrogen chloride (110 g) was bubbled through a solution of 3,4,5-trimethoxyphenyl-α-acetoxyacetonitrile (100 g) in anhydrous methanol (1000 ml) for 50 minutes at 15° C. After standing at room temperature for two hours, the mixture was concentrated to dryness. The residue was stirred with water (750 ml) for two hours, after which sodium hydroxide (100 g) was added and the stirring continued over night. The mixture was acidified with concentrated hydrochloric acid, saturated with sodium chloride and extracted with ethyl acetate (3×250 ml). The organic phase was dried and concentrated to dryness, leaving crude 3,4,5-trimethoxymandelic acid (92.5 g). Crystallization from toluene gave the pure product (86.9 g), m.p. 119-123° C.

4. 3,4,5-Trimethoxymandelic acid (80.5 g) was treated with acetyl chloride (150 ml) at room temperature for three hours. The clear solution was concentrated to dryness under vacuum, and the oily residue was crystallized from toluene (280 ml) giving pure α-acetoxy-3,4,5-trimethoxyphenylacetic acid (80.9 g), m.p. 135-139° C.

5. A solution of α-acetoxy-3,4,5-trimethoxyphenyl-acetic acid (5.0 g) in dichloromethane (40 ml) was reacted with 1,1'-carbonyldiimidazole (2.92 g) at room temperature for 30 minutes. The solution was refluxed for 30 minutes, after which N-methyl-3,4-ethylenedioxybenzylamine (3.26 g) dissolved in dichloromethane (10 ml) was added. The mixture was stirred at room temperature for 2 hours, after which it was washed with aqueous hydrochloric acid (20 ml, 1M) followed by aqueous sodium hydrogen carbonate (20 ml, 0.5 M). The organic phase was dried and concentrated to dryness, leaving crude 2-(3,4,5-trimethoxyphenyl)-2-acetoxy-N-methyl-N-3,4-ethylenedioxybenzylacetamide (7.27 g).

6. A solution of the amide from step 4 above (6.2 g) in dichloromethane (60 ml) and trifluoroacetic acid (20 ml) was refluxed for 6 hours. The reaction mixture was concentrated to dryness and the residue was crystallized from methanol, giving 2-methyl-4-(3,4,5-trimethoxyphenyl)-6,7-ethylenedioxy-1,4-dihydro-3(2H)-isoquinolinone (4.8 g), m.p. 148-149° C.

Compound 11: 2-methyl-4-(3,5-dichlorophenyl)-7-methoxy-1,4-dihydro-3(2H)-isoquinolinone 1. 3,5-Dichloromandelic acid (22.0 g, m.p. 99-104° C., from toluene), produced according to General Methods, was dissolved in methanol (500 ml) containing 5% w/w of hydrogen chloride. After standing at room temperature for 20 hours, the mixture was concentrated to dryness. The residual crude methyl 3,5-dichloromandelate was used in the next step without further purification.

2. Methanesulfonyl chloride (9.3 g) was added at 0° C. to a solution of methyl 3,5-dichloromandelate (19.0 g) and triethylamine (8.2 g) in dichloromethane (150 ml). After the addition, the mixture was stirred at room temperature for 3 hours, after which water (150 ml) was carefully added. The organic phase was separated, dried and concentrated to dryness, giving methyl 2-(3,5-dichlorophenyl)-2-mesyloxy-acetate (23.6 g) as an oil.

3. A solution of methyl 2-(3,5-dichlorophenyl)-2-mesyloxyacetate (8.2 g) in dimethylformamide (30 ml) was treated with potassium bromide (4.0 g) at 50° C. for 1.5 hours. The reaction mixture was partitioned between water (200 ml) and ethyl acetate (300 ml). The organic phase was separated and washed twice with water (2×200 ml) and finally with saturated brine solution (200 ml). The ethyl acetate solution was dried and concentrated to dryness giving crude methyl 2-(3,5-dichlorophenyl)-2-bromoacetate (8 g). Filtration through a column of silica gel using dichloromethane as eluent gave the pure substance as an oil (7.4 g).

4. A mixture of benzenethiol (2.66 g) and potassium hydroxide (1.56 g) in dioxane (200 ml) was heated at 90° C. for one hour under nitrogen. After cooling down to 20° C., a solution of methyl 2-(3,5-dimethoxyphenyl)-2-bromoacetate (7.2 g) in dioxane (50 ml) was added and the mixture was refluxed for two hours. Additionally potassium hydroxide (1.5 g) was added and the reflux continued for further two hours. After cooling to room temperature, the suspension was filtered and the filtrate concentrated to dryness. The residue was partitioned between dichloromethane (300 ml) and aqueous hydrochloric acid (1M, 300 ml). The organic phase was dried and concentrated to dryness, leaving crude 2-(3,5-dichlorophenyl)-2-(phenylsulfanyl)acetic acid. The crude product was chromatographed on silica gel using dichloromethane, followed by ethyl acetate as eluent. The fraction containing the product of interest was concentrated to dryness, and the residue was crystallized from diethyl ether/hexane giving pure 2-(3,5-dichlorophenyl)-2-(phenyl-sulfanyl)acetic acid (4.5 g), m.p. 115-119° C.

5. A solution of 2-(3,5-dichlorophenyl)-2-(phenyl-sulfanyl)acetic acid (1.65 g) in dichloromethane (50 ml) was treated with 1,1'-carbonyldiimidazole (0.90 g) at room temperature for 2 hours. A solution of N-methyl-3-methoxybenzylamine (1.0 g) in dichloromethane (15 ml) was added and the stirring was continued for one hour. The reaction mixture was washed with aqueous hydrochloric acid (1M, 50 ml) and aqueous sodium hydroxide (1M, 50 ml). The organic phase was dried and concentrated to dryness leaving crude N-(3-methoxy-benzyl)-N-methyl-2-(3,5-dichlorophenyl)-2-(phenylsulfanyl)-acetamide (1.8 g) as a viscous oil.

6. A mixture of the acetamide derivative from step 5 above (1.5 g), sodium metaperiodate (1.15 g), methanol (30 ml) and water (20 ml) was heated under reflux for 2 hours. The reaction mixture was filtered and the filtrate concentrated to dryness. The residue was purified by chromatography on silica gel using ethyl acetate as eluent, giving N-(3-methoxybenzyl)-N-methyl-2-(3,5-dichlorophenyl)-2-(phenylsulfinyl)acetamide (1.2 g) as a viscous oil.

7. Trifluoroacetic anhydride (1.5 ml) was added to a solution of N-(3-methoxybenzyl)-N-methyl-2-(3,5-dichlorophenyl)-2-(phenylsulfinyl)acetamide (1.0 g) in tetrahydrofuran (30 ml). The reaction mixture was stirred at room temperature for 15 minutes, after which it was concentrated to dryness. The crude 2-methyl-4-(3,5-dichlorophenyl)-4-(phenylsulfanyl)-7-methoxy-1,4-dihydro-3(2H)-isoquinolone was used as such without further purification in the next step below.

8. A solution of 2-methyl-4-(3,5-dichlorophenyl)-4-(phenylsulfanyl)-7-methoxy-1,4-dihydro-3(2H)-isoquinolone (1.0 g) and nickel chloride hexahydrate (3.8 g) in methanol-tetrahydrofuran (3:1, 50 ml) was cooled to 0° C. Sodium borohydride (0.66 g) was added in small portions during 30 minutes at a temperature not exceeding 5° C. The slurry was filtered and the filtrate concentrated to dryness. The residue was partitioned between dichloromethane (200 ml) and aqueous sodium hydroxide (2M, 200 ml). The organic phase was dried and concentrated to dryness leaving crude 2-methyl-4-(3,5-dichlorophenyl)-7-methoxy-1,4-dihydro-3(2H)-isoquino-linone (0.7 g). The crude product was purified by chromatography on silica gel using a mixture of dichloromethane and ethyl acetate (8:2) as eluent. Crystallization from methanol afforded the pure title compound, m.p. 163-165° C.

Compound 12: 2-amino-4-(3,4,5-trimethoxyphenyl)-7-methoxy-1,4-dihydro-3(2H)-isoquinolinone 1. A solution of 3-methoxybenzaldehyde (27.0 g) and t-butyl carbazate (25.0 g) in tetrahydrofuran (350 ml) was refluxed for 4 hours. The reaction mixture was concentrated to dryness giving t-butyl 3-methoxybenzylidenecarbazate (48.8 g) as an oil, which was used without further purification.

2. A solution of sodium dihydrido-bis(2-methoxy-ethoxy) aluminate (66 ml of a 3.5 M solution in toluene) in tetrahydrofuran (15 ml) was added to t-butyl 3-methoxy-benzylidenecarbazate (28.8 g) dissolved in tetrahydrofuran (200 ml) at 20° C. during 45 minutes. After the addition the solution was stirred at room temperature for 3 hours. The reaction mixture was treated carefully with aqueous sodium hydroxide (40 ml, 5%), after which water (200 ml) and ethyl acetate (500 ml) were added. The organic phase was separated, dried and concentrated to dryness giving t-butyl 3-methoxy-benzylcarbazate (28 g) as an oil.

3. A solution of 3,4,5-trimethoxy-α-acetyloxyacetic acid (2.3 g) in dichloromethane (20 ml) was reacted with 1,1'-carbonyldiimidazole (1.1 g) at room temperature for 30 minutes. The resulting clear solution was reflux for 30 minutes, after which t-butyl 3-methoxybenzylcarbazate (1.3 g) dissolved in dichloromethane (5 ml) was added. The mixture was stirred at room temperature for 24 hours, after which it was washed with aqueous hydrochloric acid (20 ml, 1M) followed by aqueous sodium hydrogen carbonate (20 ml, 0.5 M). The organic phase was dried and concentrated to dryness. The residue was purified by chromatography on silica gel (dichloromethane/ethyl acetate 8/2), giving 2-(3,4,5-trimethoxyphenyl)-2-acetoxy-N-(t-butyl carbamate)-N-(3-methoxybenzylacetamide (1.5 g) as an oil.

4. The acetamide (1.4 g) from step 3 above was dissolved in trifluoroacetic acid (15 ml) and the solution was kept at 40° C. for 5 hours. The reaction mixture was concentrated to dryness, and the residue partitioned between aqueous hydrochloric acid (50 ml, 2 M) and ethyl acetate (50 ml). The aqueous phase was made alkaline with sodium hydroxide and extracted with dichloromethane (2×50 ml). The organic phase was dried and concentrated to dryness, giving the title compound as pale yellow solid (0.97 g). The amine was converted to the hydrochloride, which was crystallized from methanol, giving 2-amino-4-(3,4,5-trimethoxyphenyl)-7-methoxy-1,4-dihydro-3(2H)-isoquinolinone hydrochloride, m.p. 164-167° C.

Compound 13: 2-methyl-4-(3,5-dimethoxyphenyl)-7-methoxy-1,4-dihydro-3(2H)-isoquinolinone 1. 3,5-Dimethoxymandelic acid (22.0 g, m.p. 141-145° C., from toluene), produced according to General Methods, was dissolved in methanol (500 ml) containing 5% w/w of hydrogen chloride. After standing at room temperature for 20 hours, the mixture was concentrated to dryness. The residual crude methyl 3,5-dimethoxymandelate was dissolved in dry diethyl ether (100 ml) and treated with phosphorous tribromide (13.3 g) at 0° C. After the addition, the mixture was stirred at is room temperature for 2 hours. The reaction was quenched by the addition of ice-water (200 ml) and dichloromethane (200 ml). The organic phase was dried and concentrated to dryness, leaving crude methyl 2-(3,5-dimethoxyphenyl)-2-bromoacetate.

2. A mixture of benzenethiol (5.91 g) and potassium hydroxide (3.48 g) in dioxane (200 ml) was heated at 80° C. for one hour under nitrogen. After cooling down to 20° C., a solution of methyl 2-(3,5-dimethoxyphenyl)-2-bromoacetate (15.0 g) in dioxane (100 ml) was added and the mixture was refluxed for two hours. Additionally potassium hydroxide (1.5 g) was added and the reflux continued for further two hours. After cooling to room temperature, the suspension was filtered and the filtrate concentrated to dryness. The residue was partitioned between dichloromethane (300 ml) and aqueous hydrochloric acid (1M, 300 ml). The organic phase was dried and concentrated to dryness, leaving crude 2-(3,5-dimethoxyphenyl)-2-(phenylsulfanyl)acetic acid. Crystallization from diethyl ether gave the pure compound (7.2 g), m.p. 124-126° C.

3. A solution of 2-(3,5-dimethoxyphenyl)-2-(phenyl-sulfanyl)acetic acid (6.0 g) in dichloromethane (50 ml) was treated with 1,1'-carbonyldiimidazole (3.24 g) at room temperature for 2 hours. A solution of N-methyl-3-methoxy-benzylamine (3.4 g) in dichloromethane (15 ml) was added and the stirring was continued for one hour. The reaction mixture was washed with aqueous hydrochloric acid (1M, 50 ml) and aqueous sodium hydroxide (1M, 50 ml). The organic phase was dried and concentrated to dryness leaving crude N-(3-methoxybenzyl)-N-methyl-2-(3,5-dimetoxyphenyl)-2-(phenylsulfanyl)-acetamide (9.1 g) as a viscous oil.

4. A mixture of the acetamide derivative from step 3 above (4.1 g), sodium metaperiodate (3.3 g), methanol (50 ml) and water (30 ml) was heated under reflux for 1.5 hours. The reaction mixture was filtered and the filtrate concentrated to dryness. The residue was purified by chromatography on silica gel using ethyl acetate as eluent, giving N-(3-methoxybenzyl)-N-methyl-2-(3,5-dimetoxyphenyl)-2-(phenylsulfinyl)acetamide (2.7 g) as a viscous oil.

5. Trifluoroacetic anhydride (3.9 ml) was added to a solution of N-(3-methoxybenzyl)-N-methyl-2-(3,5-dimethoxyphenyl)-2-(phenylsulfinyl)acetamide (2.6 g) in tetrahydrofuran (30 ml). The reaction mixture was stirred at room temperature for 10 minutes, after which it was concentrated to dryness. The crude 2-methyl-4-(3,5-dimethoxyphenyl)-4-

(phenylsulfanyl)-7-methoxy-1,4-dihydro-3(2H)-isoquinolone was used as such without further purification in the next step below.

6. A solution of 2-methyl-4-(3,5-dimethoxyphenyl)-4-(phenylsulfanyl)-7-methoxy-1,4-dihydro-3(2H)-isoquinolone (2.4 g) and nickel chloride hexahydrate (8.8 g) in methanol-tetrahydro-furan (3:1, 100 ml) was cooled to 0° C. Sodium borohydride (4.2 g) was added in small portions during 30 minutes at a temperature not exceeding 5° C. The slurry was filtered and the filtrate concentrated to dryness. The residue was partitioned between dichloromethane (200 ml) and aqueous sodium hydroxide (2M, 200 ml). The organic phase was dried and concentrated to dryness leaving crude 2-methyl-4-(3,5-dimethoxyphenyl)-7-methoxy-1,4-dihydro-3(2H)-isoquinolinone (1.3 g). Crystallization from methanol afforded the pure compound, m.p. 137-139

Compound 15: (+)-2-methyl-4-(3,4,5-trimethoxyphenyl)-8-hydroxy-7-methoxy-1,4-dihydro-3(2H)-isoquinolinone 1. Methylamine hydrochloride (67.5 g), sodium hydroxide (26.8 g) and dry molecular sieve (3×3 mm, 3 A, 50 g) were added to a solution of 2-isopropoxy-3-methoxybenz-aldehyde (119.4 g) in methanol (800 ml). After stirring at room temperature for 20 hours, the solution was cooled to 0° C. prior to addition of sodium borohydride (18.0 g) portion wise. The resulting solution was stirred at room temperature for one hour, after which it was concentrated to dryness. The residue was partitioned between dichloromethane (700 ml) and an aqueous solution of sodium hydroxide (400 ml, 2M). The dichloromethane phase was separated and extracted with hydrochloric acid (2×400 ml, 2M). The aqueous phase was made alkaline (pH 11-12) and extracted with dichloromethane (2×400 ml). The organic phase was dried (sodium sulphate) and concentrated to dryness, leaving 2-isopropoxy-3-methoxy-N-methylbenzylamine (97.1 g), which was used without further purification.

2. A solution of α-acetoxy-3,4,5-trimethoxyphenyl-acetic acid (5.0 g) in dichloromethane (40 ml) was reacted with 1,1'-carbonyldiimidazole (2.92 g) at room temperature for 30 minutes. The solution was refluxed for 30 minutes, after which 2-isopropoxy-3-methoxy-N-methylbenzylamine (3.26 g) dissolved in dichloromethane (10 ml) was added. The mixture was stirred at room temperature for 2 hours, after which it was washed with aqueous hydrochloric acid (20 ml, is 1M) followed by aqueous sodium hydrogen carbonate (20 ml, 0.5 M). The organic phase was dried and concentrated to dryness, leaving crude 2-(3,4,5-trimethoxyphenyl)-2-acetoxy-N-methyl-N-(2-isopropoxy-3-methoxybenzyl)acetamide (7.27 g).

3. A solution of the amide from step 2 above (6.2 g) in dichloromethane (60 ml) and trifluoroacetic acid (20 ml) was refluxed for 6 hours. The reaction mixture was concentrated to dryness and the residue was crystallized from methanol, giving 2-methyl-4-(3,4,5-trimethoxyphenyl)-8-isopropoxy-7-methoxy-1,4-dihydro-3(2H)-isoquinolinone (4.8 g), m.p. 128-129° C.

4. The pure R and S enantiomers of 2-methyl-4-(3,4,5-trimethoxyphenyl)-8-isopropoxy-7-methoxy-1,4-dihydro-3(2H)-isoquinolinone were isolated by preparative HPLC on Chiralcel OD-I CSP (20 μM, 25×250 mm) using t-butyl methyl ether and dichloromethane (8:2) as eluent. The two enantiomers were recovered as amorphous solids.

5. The two enantiomers (each 0.90 g) were separately dissolved in dichloromethane (50 ml) and treated with borontrichloride (1M, 6 ml) at 0° C. for 5 minutes. After stirring at room temperature for 30 minutes, ice-water (100 ml) and dichloromethane (100 ml) were added. The organic phase was separated, dried and concentrated to dryness. The residue was crystallized from methanol, giving the title compound, m.p. 193-196° C., $[\alpha]_D^{20}$ +17.1°, c=0.75, (CHCl$_3$) and the levorotatory enantiomer, m.p. 192-195° C., $[\alpha]_D^{20}$ −16.8°, c=0.75, (CHCl$_3$).

Compound 16: 2-methyl-4-(3,4,5-trimethoxyphenyl)-7-methoxy-1,2,3,4-tetrahydroisoquinoline A solution of sodium dihydrido-bis(2-methoxy-ethoxy) aluminate (Red-Al, 66 ml of a 3.5 M solution in toluene) was added to 2-methyl-4-(3,4,5-trimethoxyphenyl)-7-methoxy-1,4-dihydro-3(2H)-isoquinolinone (2.4 g, compound I) dissolved in tetrahydrofuran (100 ml) at 20° C. After the addition the solution was refluxed for 6 hours. The reaction mixture was treated carefully with aqueous sodium hydroxide (40 ml, 5%), after which water (100 ml) and ethyl acetate (200 ml) were added. The organic phase was separated, dried and concentrated to dryness. The residue was converted into the hydrochloride, which was crystallized from methanol, giving the hydrochloride of the title compound, m.p. 201-204° C.

Compound 17: 1,2-Dimethyl-4-(3,4,5-trimethoxyphenyl)-7-methoxy-1,4-dihydro-3(2H)-isoquinolinone 1. Titanium(IV) isopropoxide (130 ml) was added to a methanolic methylamine solution (125 ml, 8M) followed by the addition of 3-methoxybenzophenone (50 g). The reaction mixture was stirred at room temperature for 5 hours, after which sodium borohydride (12 g) was carefully added at 0-5° C. The mixture was stirred at room temperature for 2 hours, after which water (60 ml) was added. The inorganic precipitate was filtered off and the filtrate concentrated to dryness. The residue was partitioned between ethyl acetate (400 ml) and aqueous hydrochloric acid (2M, 400 ml). The aqueous phase was made alkaline (pH 11-12) and extracted with dichloromethane (2×300 ml). The organic phase was dried and concentrated to dryness, leaving 1-(3-methoxyphenyl)-N-methylethylamine (43.4 g) as a viscous oil.

2. A solution of α-acetoxy-3,4,5-trimethoxyphenyl-acetic acid (7.1 g) in dichloromethane (50 ml) was reacted with 1,1'-carbonyldiimidazole (4.06 g) at room temperature for 30 minutes. The solution was refluxed for 30 minutes, after which 1-(3-methoxyphenyl)-N-methylethylamine (4.13 g) dissolved in dichloromethane (10 ml) was added. The mixture was stirred at room temperature for 2 hours, after which it was washed with aqueous hydrochloric acid (20 ml, 1M) followed by aqueous sodium hydrogen carbonate (20 ml, 0.5 M). The organic phase was dried and concentrated to dryness, leaving crude 2-(3,4,5-trimethoxyphenyl)-2-acetoxy-N-methyl-N-[1-(3-methoxyphenyl)ethyl]acetamide (7.27 g).

3. A solution of the amide from step 2 above (4.2 g) in dichloromethane (60 ml) and trifluoroacetic acid (20 ml) was refluxed for 4 hours. The reaction mixture was concentrated to dryness and the residue was submitted to chromatography on silica gel using dichloromethane-ethyl acetate (6:4) as eluent. The first fraction was concentrated to dryness and the residue was crystallized from methanol giving diastereomer I, m.p. 135-140° C. The third fraction contained diastereomer II, which was recovered as an amorphous solid.

Compound 18: 2-cyano-4-(3,4,5-trimethoxyphenyl)-7-methoxy-1,2,3,4-tetrahydroisoquinoline 1. A solution of compound 16 (1.8 g) and cyanogen bromide (1.0 g) was refluxed for 6 hours. The solution was is evaporated to dryness and the residue partitioned between dichloromethane (100 ml) and aqueous hydrochloric acid (2M, 100 ml). The organic phase was dried and concentrated to dryness. The residue was crystallized from methanol giving the title compound (0.7 g), m.p. 113-116° C.

Biological Data

Example 19

Cell Growth Inhibition Study on Human Cancer Cell Lines Jurkat, MCF-7 and SK-MEL 28

MCF-7 and SK-MEL 28 cells (~3000 cells/200 μl) were transferred into 96 well plates and grown, with or without the test compounds, for 48 hours at 37° C. in RPMI medium (Gibco) supplemented with 10% fetal calf serum containing penicillin, streptomycin and fungizone (Amimed Ltd.). The same procedure was followed for Jurkat cells, except for the density of cells (~50000 cells/200 μl) and that the incubation time was limited to 24 hours. At the end of the incubation times, the cell growth inhibition of the Jurkat, SK-MEL 28 and MCF-7 cell lines were determined by the use of an MTT test (Sigma). The compounds of the examples were found to have in the above tests an $IC_{50}$ of from 8 microgram/ml to 3 nanogram/ml in at least one cell line.

Example 20

Inhibition of the Phosphorylation of the IGF-1 Receptor in MCF-7 Cells by Compound 15

MCF-7 cells were serum starved for 20 hours, treated with compound 15 for 3 hours and finally stimulated with 10 nM IGF-1 for 5 minutes. The cells were lyzed and the lysates analysed by SDS-PAGE and immunoblotting for phospho-IGF-1R is (Y1135/1136). It was found that the phosphorylation of the IGF-1 receptor was inhibited by the presence of compound 15 in a dose dependant manner with an $IC_{50}$ of around 1 μM.

Example 21

Inhibition of the Phosphorylation of Insulin Receptor Substrate 1 (IRS-1) in MF-55 Cells by Racemic Compound 15

MF-55 cells (malignant melanoma) were starved for 20 hours, after which half of the cell mass was incubated with racemic compound 15 (100 ng/ml) for one hour. After activation with IGF-1 (50 ng/ml) for 5 minutes, the two cell samples were lyzed in a special buffer (Upstate Ltd., Dundee, UK) that disrupts the cell membrane as well as the nucleus envelope. After removal of cell debris by centrifugation, the supernatants were analyzed for phosphorylated IRS-1 by Upstate Ltd. The presence of racemic compound 15 lowered the amount of phosphorylated IRS-1 with 20% compared to control. By blocking the function of the IGF-1 receptor, the phosphorylation of the insulin receptor substrate 1 is inhibited.

Example 22

Inhibition of the Phosphorylation of MAPK in DU-145 Cells by Compound 15

DU-145 cells (prostate cancer) were incubated over night with compound 15 in serum free medium. After stimulation for 15 minutes with IGF1 (50 nM), the cells were lyzed and the lysates analysed by immunoblotting for phospho-MAPK. It was found that the phosphorylation of MAPK (Erk1/2) was inhibited by the presence of compound 15 in a dose dependant manner with an $IC_{50}$ of around 0.3 μM. Picropodophyllin, used as a standard, showed an $IC_{50}$ of around 5 μM.

The invention claimed is:
1. A compound of the following formula (I):

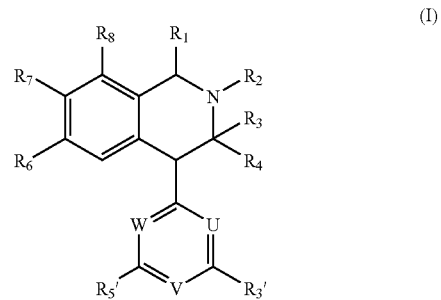

wherein, $R_1$ designates hydrogen; OH; CN; trifluoromethyl; $NH_2$; NHCN; $NHCOCH_3$; $NHCOCH_2CH_3$; NHCHO; $NHCOOCH_3$; amino($C_1$-$C_6$)alkyl; amino($C_1$-$C_3$)dialkyl; ($C_1$-$C_6$)alkoxy; ($C_1$-$C_6$)alkyl; carbonyl-$R_9$ wherein $R_9$ designates hydrogen, ($C_1$-$C_6$)alkyl, ($C_1$-$C_6$)alkoxy; ($C_1$-$C_6$) alkyl-$R_{10}$; ($C_1$-$C_6$)alkoxy-$R_{10}$; amino ($C_1$-$C_6$)alkyl-$R_{10}$ and amino($C_1$-$C_3$)dialkyl-$R_{10}$ whereby $R_{10}$ designates at least one OMe, OEt, OPr, OIsopropyl, OH, CN, $NH_2$, ester groups with ($C_1$-$C_3$) alkyl, carbonate groups with ($C_1$-$C_3$)alkyl;

$R_2$ designates (when $R_3$, $R_4$ forms a carbonyl group) hydrogen; ($C_1$-$C_6$)alkyl; $CH_2CH_2N(CH_3)_2$; $NH_2$; $NHCH_3$; $N(CH_3)_2$; NHCN; $NHCOCH_3$; $NHCOCH_2CH_3$; NHCHO; $NHCOOCH_3$;

$R_2$ designates (when $R_3$=$R_4$=H) hydrogen; ($C_1$-$C_6$) alkyl; CN; CHO; $COOCH_3$; $COOCH_2CH_3$; $COCH_3$;

$R_3$ and $R_4$ designate hydrogen, or $R_3$ and $R_4$ taken together form a carbonyl group;

$R_6$ designates hydrogen, or $R_6$ and $R_7$ taken together form a methylenedioxy group or an ethylenedioxy group;

$R_7$ designates Me; ($C_1$-$C_4$)alkoxy; ($C_1$-$C_2$)alkoxy partly or fully fluorinated, $OCF_3$; trifluoromethyl; SMe; SEt or $R_7$ and $R_8$ taken together form a methylenedioxy group or an ethylenedioxy group;

$R_8$ designates hydrogen; ($C_1$-$C_4$)alkyl; OH; ($C_1$-$C_4$) alkoxy; ($C_1$-$C_2$)alkoxy partly or fully fluorinated; $OCF_3$; trifluoromethyl; halogen or OX;

$R_3'$ and $R_5'$ each independently designate OH; Me; Et; OMe; OMe partly or fully fluorinated; $OCF_3$; trifluoromethyl or halogen;

U designates N or $CR_2'$, whereby $R_2'$ denotes hydrogen, ($C_1$-$C_4$)alkyl; ($C_1$-$C_4$)alkoxy; trifluoromethyl or halogen;

V designates N or $CR_4'$, whereby $R_4'$ denotes hydrogen; ($C_1$-$C_6$)alkoxy; ($C_1$-$C_4$)alkoxy partly or fully fluorinated; ($C_1$-$C_6$)alkyl; OH; trifluoromethyl; halogen or OX;

W designates N or $CR_6'$, whereby $R_6'$ denotes hydrogen; ($C_1$-$C_4$)alkyl; ($C_1$-$C_4$)alkoxy; trifluoromethyl or halogen;

wherein OX designates a group capable of conferring a prodrug property, said group being selected among phosphate derivatives, ester derivatives, carbonate derivatives and/or linked poly(ethylene glycols) derivatives;

or pharmaceutically acceptable salt thereof, provided that when:

$R_1$ is H, $R_2$ and $R_7$ are Me, $R_8$ and $R_4'$ are H, $R_5'$ must be different from F or Cl; or $R_1$, $R_2$ and $R_7$ are Me, $R_8$ and $R_4'$ are H, $R_5'$ must be different from F; or $R_1$ is H, $R_2$ and $R_7$ are Me, $R_8$ is H and $R_4'$ is F, $R_5'$ must be different from F.

2. The compound according to claim 1, wherein $R_3$ and $R_4$ taken together form a carbonyl group.

3. The compound according to claim 1, wherein $R_1$ designates hydrogen or $(C_1$-$C_6)$alkyl and $R_2$ designates hydrogen; $(C_1$-$C_6)$alkyl; $CH_2CH_2N(CH_3)_2$; $NH_2$; $NHCH_3$; $N(CH_3)_2$; NHCN; $NHCOCH_3$; $NHCOCH_2CH_3$; NHCHO or $NHCOOCH_3$.

4. The compound according to claim 1, wherein $R_7$ designates OMe, $OCHF_2$ or OEt.

5. The compound according to claim 1 wherein $R_8$ designates OH; OMe; halogen or OX.

6. The compound according to claim 1, wherein $R_7$ designates OMe, $OCHF_2$ or OEt and $R_8$ designates OH; OMe; halogen or OX.

7. The compound according to claim 1, wherein $R_3'$ and $R_5'$ each independently designate chloro; bromo; Me; $OCHF_2$ or OMe.

8. The compound according to claim 1, wherein $R_3'$ and $R_5'$ are identical.

9. The compound according to claim 8, wherein $R_3'$ and $R_5'$ designate chloro or bromo or $OCHF_2$.

10. The compound according to claim 1, wherein U and W designate CH and V designates $CR_4'$.

11. The compound according to claim 10, wherein $R_4'$ designates hydrogen; chloro; bromo; Me; OMe; $OCHF_2$ or OX.

12. The compound according to claim 10, wherein $R_3'$, $R_4'$ and $R_5'$ designate OMe; or $R_3'$ designates chloro and $R_4'$ and $R_5'$ designate OMe; or $R_4'$ designates hydrogen and $R_3'$ and $R_5'$ both designate chloro and bromo or $OCHF_2$.

13. The compound according to claim 1, which is the 4-(R) or 4-(S) enantiomer.

14. The compound according to claim 1, wherein pharmaceutically acceptable salt is produced from acidic inorganic or organic compounds, or alkaline inorganic or organic compounds.

15. The compound according to claim 2, wherein $R_1$ designates hydrogen or $(C_1$-$C_6)$alkyl and $R_2$ designates hydrogen; $(C_1$-$C_6)$alkyl; $CH_2CH_2N(CH_3)_2$; $NH_2$; $NHCH_3$; $N(CH_3)_2$; NHCN; $NHCOCH_3$; $NHCOCH_2CH_3$; NHCHO or $NHCOOCH_3$.

16. A medicament, comprising the compound according to claim 1.

17. A pharmaceutical composition, comprising: the compound of formula (I), or the pharmaceutically acceptable salt thereof, according to claim 1, and a pharmaceutically acceptable adjuvant, diluent or carrier.

18. A pharmaceutical composition, comprising: the compound of formula (I), or the pharmaceutically acceptable salt thereof according to claim 2, and a pharmaceutically acceptable adjuvant, diluent or carrier.

19. A method of treatment or prophylaxis of leukemia, breast cancer, melanoma cancer or prostate cancer in which down-regulation or inhibition of the expression or function of the IGF-1 receptor is beneficial, in a subject in need thereof, comprising:

administering, to the subject, the compound of formula (I) according to claim 1 in an amount which is effective in down-regulating or inhibiting the expression or function of the IGF-1 receptor.

20. A method of evaluating the effects of inhibitors interfering with cell division by blocking cells in prophase of the mitotic cycle, comprising:

utilizing the compound according to claim 1 as a pharmacological tool in the development and standardization of in vitro and in vivo test systems for the cells.

21. A method of treatment or prophylaxis of leukemia, breast cancer, melanoma cancer or prostate cancer in which down-regulation or inhibition of the expression or function of the IGF-1 receptor is beneficial, in a subject in need thereof, comprising:

administering, to the subject, the compound of formula (I) according to claim 2 in an amount which is effective in down-regulating or inhibiting the expression or function of the IGF-1 receptor.

22. A method of evaluating the effects of inhibitors interfering with cell division by blocking cells in prophase of the mitotic cycle, comprising:

utilizing the compound according to claim 2 as a pharmacological tool in the development and standardization of in vitro and in vivo test systems for the cells.

23. A kit, comprising:

the compound of formula (I) or the pharmaceutically acceptable salt thereof according to claim 1, and a chemotherapeutic agent, as a combination for the simultaneous, separate or successive administration in the therapy of a disease in which down-regulation or inhibition of the expression or function of the IGF-1 receptor is beneficial.

24. A kit, comprising:

the compound of the formula (I) or the pharmaceutically acceptable salt thereof according to claim 2, and a chemotherapeutic agent, as a combination for the simultaneous, separate or successive administration in the therapy of a disease in which down-regulation or inhibition of the expression or function of the IGF-1 receptor is beneficial.

* * * * *